US009267067B2

(12) United States Patent
Yang et al.

(10) Patent No.: US 9,267,067 B2
(45) Date of Patent: Feb. 23, 2016

(54) HEAT TRANSFER FLUID, ADDITIVE PACKAGE, SYSTEM AND METHOD

(71) Applicant: PRESTONE PRODUCTS CORPORATION, Lake Forest, IL (US)

(72) Inventors: Bo Yang, Ridgefield, CT (US); Aleksei V. Gershun, Southbury, CT (US); Peter M. Woyciesjes, Woodbury, CT (US)

(73) Assignee: Prestone Products Corporation, Lake Forest, IL (US)

( * ) Notice: Subject to any disclaimer, the term of this patent is extended or adjusted under 35 U.S.C. 154(b) by 17 days.

(21) Appl. No.: 14/325,990

(22) Filed: Jul. 8, 2014

(65) Prior Publication Data
US 2014/0319409 A1 Oct. 30, 2014

Related U.S. Application Data

(62) Division of application No. 12/500,220, filed on Jul. 9, 2009, now Pat. No. 8,771,542.

(60) Provisional application No. 61/080,011, filed on Jul. 11, 2008.

(51) Int. Cl.
C09K 5/20 (2006.01)
C23F 11/10 (2006.01)
C09K 5/10 (2006.01)
C23F 11/12 (2006.01)
C07C 59/245 (2006.01)
C07C 59/48 (2006.01)

(52) U.S. Cl.
CPC ............... C09K 5/20 (2013.01); C07C 59/245 (2013.01); C07C 59/48 (2013.01); C09K 5/10 (2013.01); C23F 11/10 (2013.01); C23F 11/124 (2013.01)

(58) Field of Classification Search
CPC .......... C09K 5/20; C23F 11/10; C23F 11/124
USPC ................. 252/79, 71, 78.1, 78.3, 67, 68, 69; 165/186
See application file for complete search history.

(56) References Cited

U.S. PATENT DOCUMENTS

| 3,169,139 A | 2/1965 | D'Addieco |
| 3,198,820 A | 8/1965 | Pines et al. |
| 3,203,969 A | 8/1965 | Pines et al. |
| 3,248,329 A | 4/1966 | Pines et al. |
| 3,312,622 A | 4/1967 | Pines et al. |
| 3,337,496 A | 8/1967 | Pines et al. |
| 3,341,469 A | 9/1967 | Pines et al. |
| 4,093,641 A | 6/1978 | Plueddemann |
| 4,241,016 A | 12/1980 | Hirozawa |
| 4,287,077 A | 9/1981 | Wing |
| 4,333,843 A | 6/1982 | Wing et al. |
| 4,352,742 A | 10/1982 | Davis et al. |
| 4,354,002 A | 10/1982 | Davis et al. |
| 4,362,644 A | 12/1982 | Davis et al. |
| 4,370,255 A | 1/1983 | Plueddemann |
| 4,517,110 A | 5/1985 | Suzuki et al. |
| 4,629,602 A | 12/1986 | Gousetis et al. |
| 4,701,277 A | 10/1987 | Mohr et al. |
| 4,772,408 A | 9/1988 | Mohr et al. |
| 4,927,669 A | 5/1990 | Knox et al. |
| 5,292,480 A | 3/1994 | Fischer et al. |
| 5,378,372 A | 1/1995 | Carey et al. |
| 5,489,666 A | 2/1996 | Carey et al. |
| 5,589,106 A | 12/1996 | Shim et al. |
| 5,616,278 A | 4/1997 | Carey et al. |
| 5,750,070 A | 5/1998 | Tang et al. |
| 5,788,857 A | 8/1998 | Yang et al. |
| 5,866,042 A | 2/1999 | Chen et al. |
| 5,871,691 A | 2/1999 | Carey et al. |
| 5,980,774 A | 11/1999 | Sapienza |
| 6,391,257 B1 | 5/2002 | Woyciesjes |
| 6,515,061 B1 | 2/2003 | Iruvanti et al. |
| 6,572,789 B1 | 6/2003 | Yang et al. |
| 6,846,431 B1 | 1/2005 | Dunuwila et al. |
| 7,229,568 B2 | 6/2007 | Sapienza |
| 8,771,542 B2 * | 7/2014 | Yang .................... C09K 5/10 252/67 |
| 2005/0012069 A1 * | 1/2005 | Maes ...................... C09K 5/08 252/73 |
| 2005/0260723 A1 | 11/2005 | Yu |

(Continued)

FOREIGN PATENT DOCUMENTS

| GB | 776757 | 6/1954 |
| GB | 769200 | 2/1957 |

(Continued)

OTHER PUBLICATIONS

International Search Report for PCT/US2009/050249, mailed Feb. 3, 2010.*
Japanese Publication No. 6228184; published Aug. 16, 1994; Abstract only; 1 page.
Decision on Appeal re Ex Parte Thomas L. Block et al.; Appeal No. 2009-005354; Nov. 30, 2010; U.S. Appl. No. 10/159,539; Publication No. 2003-008592; U.S. Pat. No. 8,361,912.
Dictionary Reference of the word "can" at http://www.merriam-webster.com/dictionary/can; Mar. 21, 2013; 4 pages.

(Continued)

Primary Examiner — Douglas Mc Ginty
(74) Attorney, Agent, or Firm — Gregory H. Zayia; Barnes & Thornburg LLP

(57) ABSTRACT

Disclosed herein is a heat transfer fluid, comprising a hydroxylated carboxylic acid of formula $(OH)_x(R1)(COOH)_y$, wherein x is 2 to 10, y is 3 to 10, and R1 is a C2-50 aliphatic group, a C6-50 aromatic group, or a combination thereof; and wherein the hydroxylated carboxylic acid comprises the hydroxylated carboxylic acid, an ester thereof, a salt thereof, an anhydride thereof, or a combination thereof. A heat transfer system comprises an aluminum component, a magnesium component, or an aluminum component and a magnesium component; and the foregoing heat transfer fluid.

26 Claims, 1 Drawing Sheet

(56) References Cited

U.S. PATENT DOCUMENTS

| | | |
|---|---|---|
| 2006/0017044 A1 | 1/2006 | Zhang et al. |
| 2006/0169399 A1 | 8/2006 | Kronzer |
| 2006/0202156 A1 | 9/2006 | Sapienza |
| 2007/0012896 A1 | 1/2007 | Sapienza |
| 2007/0063168 A1 | 3/2007 | Sapienza |
| 2007/0120094 A1 | 5/2007 | Yang et al. |
| 2008/0083900 A1 | 4/2008 | Wei et al. |

FOREIGN PATENT DOCUMENTS

| | | | |
|---|---|---|---|
| JP | 2002038137 | 2/2002 | |
| WO | 9811172 | 3/1998 | |
| WO | WO 9811172 A1 * | 3/1998 | ............... C09K 5/10 |
| WO | 0011102 | 3/2000 | |
| WO | 2004050785 | 6/2004 | |

OTHER PUBLICATIONS

Dictionary Reference of the word "can" at http://www.ldoceonline.com/dictionary/can_1; Mar. 21, 2013; 3 pages.

Written Opinion dated Feb. 3, 2010, for PCT/US2009/050249; International Filing Date Jul. 10, 2009.

International Search Report dated Feb. 23, 2010, for PCT/US2009/050249; International Filing Date Jul. 10, 2009.

* cited by examiner

HEAT TRANSFER FLUID, ADDITIVE PACKAGE, SYSTEM AND METHOD

CROSS REFERENCE TO RELATED APPLICATIONS

This application is a divisional of U.S. patent application Ser. No. 12/500,220, filed on Jul. 9, 2009, now U.S. Pat. No. 8,771,542, issued Jul. 8, 2014, which claims the benefit of U.S. Provisional Patent Application Ser. No. 61/080,011, filed on Jul. 11, 2008, the disclosures of which are incorporated by reference herein in their entirety.

BACKGROUND

This disclosure generally relates to a heat transfer fluid, additive package, system, and method.

The operation of a power source generates heat. A heat transfer system, in communication with the power source, regulates the generated heat by absorbing and dissipating the heat from the power source. A gasoline powered internal combustion engine, for example, powers an automotive vehicle. Heat transfer fluids and systems dissipate the heat generated as a by-product of gasoline combustion, and ensure that the engine operates at an optimum temperature. Heat transfer fluids, which generally comprise water or a glycol, are in communication with one or several metallic parts that are prone to corrosion. Thus, several corrosion inhibitors are added to the heat transfer fluid in order to protect the metallic parts from corrosion.

Several power sources alternative to internal combustion engines, including but not limited to batteries, fuel cells, solar or photovoltaic cells, and internal combustion engines powered by the condensation of steam, natural gas, diesel, bio diesel, alcohol, bio alcohol, hydrogen, and/or the like, also benefit from heat transfer fluids and systems. Alternative power sources can be used alone or in combination, such as in hybrid vehicles or other non-vehicle applications.

Aluminum is an example of a metal, that, along with its alloys, can be used in the manufacture of several components of the heat transfer system such as radiators, condensers, evaporators, heater cores, intercoolers, charge air coolers, oil coolers, heat exchangers, water pumps, flow channels, engine blocks, and the like.

Magnesium alloys have a high strength-to-weight ratio. Use of magnesium alloys in automobiles has been increasing due to the need of increasing fuel economy, reducing pollution and lessening dependence on petroleum. Several magnesium alloy applications in various parts of vehicles have been developed, including, but not limited to, oil pans, gearbox housings, and radiator support assemblies. However, use of magnesium alloys for vehicle powertrain systems, such as engine blocks, and for parts of a heat transfer system, has been quite limited to date. One limitation may be attributed to their poor corrosion resistance when they are in contact with the heat transfer fluids commonly used in heat transfer systems. The use of magnesium alloys in alternative power sources shares similar corrosion related drawbacks.

The aluminum and magnesium can be prone to corrosion, such as, but not limited to, cavitation corrosion, erosion corrosion, cavitation erosion corrosion, halogen based flux residue induced corrosion, galvanic corrosion, pitting corrosion, crevice corrosion, and the like. Several types of corrosion inhibitors have been identified to address the foregoing corrosions, such as organic acids, silicates, organic acid/silicate hybrids, and the like. However, common corrosion inhibitors suffer from certain drawbacks such as, but not limited to, depletion of the active corrosion inhibitor over time, excessive foaming in certain components (for example, in a water pump) which leads to premature failure due to cavitation and erosion corrosion, and lack of compatibility with different corrosion-prone metals.

Thus, there exists a need for heat transfer fluids that provide improved corrosion resistance to several metals, such as, but not limited to, aluminum and magnesium, while reducing foaming tendencies that can adversely affect components in a heat transfer system. In addition, there is an ongoing interest in corrosion inhibitors with improved corrosion inhibiting properties, and other advantageous properties such as anti-foaming, or low foaming tendency, and the like.

SUMMARY

The above-described and other drawbacks are alleviated by a heat transfer fluid comprising a hydroxylated carboxylic acid of formula (I):

$$(OH)_x(R^1)(COOH)_y, \qquad (I),$$

wherein x is 2 to 10, y is 3 to 10, and $R^1$ is a $C_{2-50}$ aliphatic group, a $C_{6-50}$ aromatic group, or a combination thereof, and wherein the hydroxylated carboxylic acid comprises the hydroxylated carboxylic acid, an ester thereof, a salt thereof, an anhydride thereof, or a combination thereof.

One embodiment is a method of treating a heat transfer fluid comprising mixing with the heat transfer fluid an additive package comprising a hydroxylated carboxylic acid of formula (I):

$$(OH)_x(R^1)(COOH)_y, \qquad (I),$$

wherein x is 2 to 10, y is 3 to 10, and $R^1$ is a $C_{2-50}$ aliphatic group, a $C_{6-50}$ aromatic group, or a combination thereof, and wherein the heat transfer fluid comprises water, an alcohol, or a combination thereof, and wherein the hydroxylated carboxylic acid comprises the hydroxylated carboxylic acid, an ester thereof, a salt thereof, an anhydride thereof, or a combination thereof.

Another embodiment is an additive package for use with a heat transfer fluid, comprising a hydroxylated carboxylic acid of formula (I):

$$(OH)_x(R^1)(COOH)_y, \qquad (I),$$

wherein x is 2 to 10, y is 3 to 10, and $R^1$ is a $C_{2-50}$ aliphatic group, a $C_{6-50}$ aromatic group, or a combination thereof, and wherein the hydroxylated carboxylic acid comprises the hydroxylated carboxylic acid, an ester thereof, a salt thereof, an anhydride thereof, or a combination thereof.

Another embodiment is a heat transfer system comprising an aluminum component, a magnesium component, or a combination thereof, and a heat transfer fluid comprising a hydroxylated carboxylic acid of formula (I):

$$(OH)_x(R^1)(COOH)_y, \qquad (I),$$

wherein x is 2 to 10, y is 3 to 10, and $R^1$ is a $C_{2-50}$ aliphatic group, a $C_{6-50}$ aromatic group, or a combination thereof, and wherein the hydroxylated carboxylic acid comprises the hydroxylated carboxylic acid, an ester thereof, a salt thereof, an anhydride thereof, or a combination thereof.

Another embodiment is a method of transferring heat comprising contacting a heat transfer system comprising an aluminum component, a magnesium component, or a combination thereof, with a heat transfer fluid comprising a hydroxylated carboxylic acid of formula (I):

$$(OH)_x(R^1)(COOH)_y, \qquad (I),$$

wherein x is 2 to 10, y is 3 to 10, and $R^1$ is a $C_{2-50}$ aliphatic group, a $C_{6-50}$ aromatic group, or a combination thereof, and wherein the hydroxylated carboxylic acid comprises the hydroxylated carboxylic acid, an ester thereof, a salt thereof, an anhydride thereof, or a combination thereof.

BRIEF DESCRIPTION OF THE DRAWINGS

Referring now to the drawings wherein like elements are numbered alike in several FIGURES.

DETAILED DESCRIPTION

Figure 1:
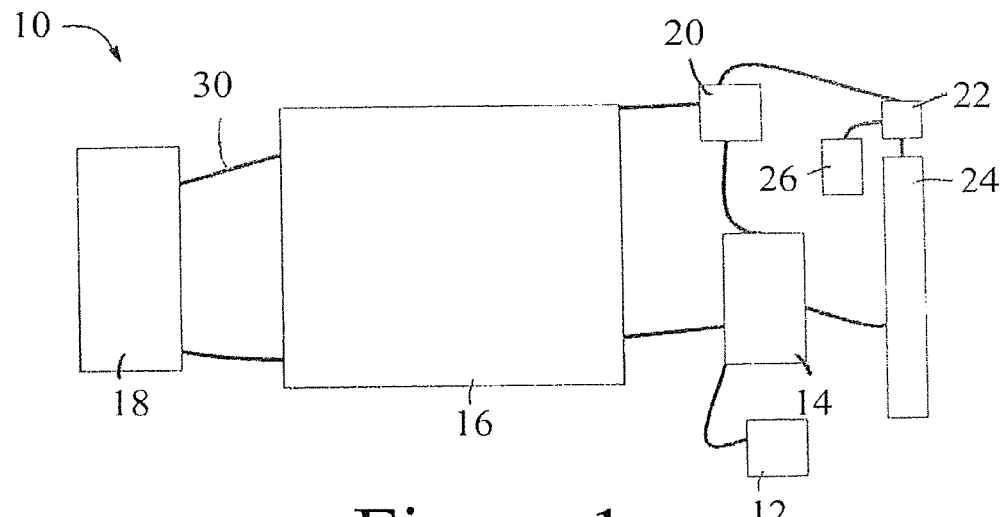
FIG. 1 is a schematic diagram of an exemplary heat transfer system.

Surprisingly, the present inventors have discovered that a heat transfer fluid, comprising a hydroxylated carboxylic acid of formula (I):

$$(OH)_x(R^1)(COOH)_y \qquad (I),$$

is effective at inhibiting the corrosion of aluminum, magnesium, and their alloys, while reducing the foaming of the heat transfer fluid. While not wishing to be bound by theory, it is believed that the reduced foaming of the heat transfer fluid further contributes to its corrosion inhibiting properties by reducing the effect of cavitation and/or erosion corrosion.

As used herein, a "hydroxylated carboxylic acid" includes the hydroxylated carboxylic acid, an ester thereof, a salt thereof, an anhydride thereof, and a combination comprising at least one of the foregoing.

As used in formula (I), x is 2 to 10, more specifically 2 to 8, more specifically 2 to 6, and even more specifically 2 to 4. In one embodiment, x is 2. As used in formula (I), y is 3 to 10, more specifically 3 to 8, more specifically 3 to 6, and even more specifically 3 to 4. In one embodiment, y is 4. R1 is a C2-50 aliphatic group or a C6-50 aromatic group. Combinations of the foregoing can also be used, such as an aliphatic group substituted with another aliphatic group, an aromatic group substituted with another aromatic group, or an aliphatic group substituted with an aromatic group (araliphatic). R1 has a total valence of (x+y).

The aliphatic group can be any group having a valence of at least one, comprising a linear or branched array of atoms, optionally substituted with substituents selected from the group consisting of lower alkyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Thus, the array can include heteroatoms such as nitrogen, sulfur and oxygen or can be composed exclusively of carbon and hydrogen. As used herein, "lower" refers to C1-6 groups.

Aliphatic groups also include cycloaliphatic groups. The cycloaliphatic groups can be any group having a valence of at least one, comprising an array of atoms which is cyclic but which is not aromatic, optionally substituted with substituents selected from the group consisting of lower alkyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkoxy, alkyl, or aryl, silyl optionally substituted by alkoxy, alkyl, or aryl, nitro, cyano, halogen, or lower perfluoroalkyl, multiple degrees of substitution being allowed. The array can include heteroatoms such as nitrogen, sulfur and oxygen or can be composed exclusively of carbon and hydrogen.

The aromatic group can be any group having a valence of at least one comprising at least one aromatic group optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

In one embodiment, the hydroxylated carboxylic acid of formula (I) is selected from a hydroxylated carboxylic acid of formula (II):

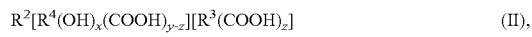

$$R^2[R^4(OH)_x(COOH)_{y-z}][R^3(COOH)_z] \qquad (II),$$

wherein $R^2$ is monovalent, $R^3$ has a total valence of (1+z), and $R^2$ and $R^3$ are independently a $C_{1-20}$ aliphatic group, $C_{6-20}$ aromatic group, or a combination thereof. $R^4$ has a total valence of (2+x+y−z), and is a $C_{2-15}$ aliphatic group, $C_{6-15}$ aromatic group, or a combination thereof. In addition, x and y are as disclosed above, and z is 1-8, with the proviso that (y-z) is greater than or equal to 2. Aliphatic groups (including cycloaliphatic groups) and aromatic groups include all the above disclosed.

In another embodiment, the hydroxylated carboxylic acid of formula (II) is selected from a hydroxylated carboxylic acid of formula (III):

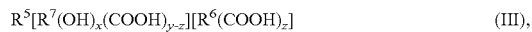

$$R^5[R^7(OH)_x(COOH)_{y-z}][R^6(COOH)_z] \qquad (III),$$

wherein $R^5$ and $[R^6(COOH)_z]$ have a total valence of 1, and are independently a $C_{1-20}$ aliphatic group selected from the group consisting of an alkyl group, an alkenyl group, a cycloalkyl group, a cycloalkenyl group, and a combination thereof. $R^6$ comprises $(COOH)_z$, that is, a z amount of carboxylic acid groups. $[R^7(OH)_x(COOH)_{y-z}]$ has a total valence of 2, and is a $C_{1-15}$ aliphatic group selected from the group consisting of an alkylene group, an alkenylene group, a cycloalkylene group, a cycloalkenylene group, and a combination thereof, having an x amount of (OH) groups and a (y-z) amount of (COOH) groups. Also, x, y, and z are as disclosed above, with the proviso that (y-z) is greater than or equal to 2.

Alkyl groups include monovalent, straight or branched chain hydrocarbon groups having from 1 to 20 carbon atoms, optionally substituted with substituents selected from the group consisting of lower alkyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Non-limiting examples of alkyl groups include methyl, n-butyl, n-pentyl, isobutyl, isopropyl, neopentyl, hexyl, heptyl, and the like.

Alkenyl groups include monovalent hydrocarbon groups having from 2 to 20 carbon atoms and at least one carbon-carbon double bond, optionally substituted with substituents selected from the group consisting of lower alkyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Non-limiting examples of alkenyl groups include vinyl, allyl, 1-propen-2-yl, isopropenyl, butenyl, 2-methyl-1-buten-3-yl, 3-methyl-2-buten-1-yl, 2,4-nonadien-2-yl, 4-sec-butyl-6-ethyl-7-methyl-3-octen-3yl, and the like.

Cycloalkyl groups include alicyclic monovalent hydrocarbon groups with one or more rings that can be separate, fused, or a combination thereof. Cycloalkyl groups have 3 to 20 carbon atoms, and are optionally substituted with substituents selected from the group consisting of lower alkyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Non-limiting examples of cycloalkyl groups include cyclopropyl, cyclobutyl, cyclopentyl, cyclohexyl, cycloheptyl, cyclooctyl, and the like.

Cycloalkenyl groups include alicyclic monovalent hydrocarbon groups with one or more rings that can be separate, fused, or a combination thereof, as well as at least one carbon-carbon double bond within a ring. Cycloalkenyl groups have 3 to 20 carbon atoms, and are optionally substituted with substituents selected from the group consisting of lower alkyl, lower alkenyl, lower alkoxy, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Non-limiting examples of cycloalkenyl groups include cyclopropenyl, cyclobutenyl, cyclopentenyl, cyclohexenyl, cycloheptenyl, cyclooctenyl, and the like.

Alkylene, alkenylene, cycloalkylene, and cycloalkenylene groups respectively include the divalent equivalent of the above disclosed alkyl, alkenyl, cycoalkyl, and cycloalkenyl groups.

In another embodiment, the hydroxylated carboxylic acid of formula (III) is selected from a hydroxylated carboxylic acid of formula (IV):

$$CH_3(CH_2)_m[R^7(OH)_x(COOH)_{y-1}](CH_2)_n(COOH) \quad (IV),$$

wherein x, and y are as disclosed above, and $[R^7(OH)_x(COOH)_{y-1}]$ is as disclosed above for $[R^7(OH)_x(COOH)_{y-z}]$, with z being 1. In addition, m and n are independently 0 to 19, more specifically 0 to 15, more specifically 0 to 10, more specifically 0 to 8, more specifically 1 to 8, and even more specifically 2 to 8. In one embodiment, m+n is less than or equal to 16. In one specific embodiment, m and n are independently 0 to 10, with the proviso that m+n is less than or equal to 16. In another specific embodiment, m and n are independently 0 to 10, with the proviso that m+n is less than or equal to 14. In another specific embodiment, m and n are independently 0 to 10, with the proviso that m+n is less than or equal to 12. In another specific embodiment, m and n are independently 0 to 10, with the proviso that m+n is 10 to 14. In another specific embodiment, m and n are independently 2 to 10, with the proviso that m+n is 10 to 14. In yet another specific embodiment, m and n are independently 2 to 8, with the proviso that m+n is 10 to 14.

In one advantageous embodiment, the hydroxylated carboxylic acid of formula (IV) is selected from the group consisting of a hydroxylated carboxylic acid of formula (V):

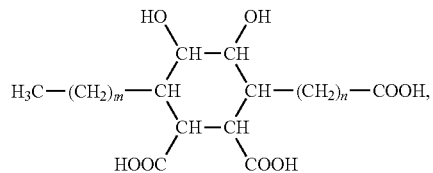

(V)

a hydroxylated carboxylic acid of formula (VI):

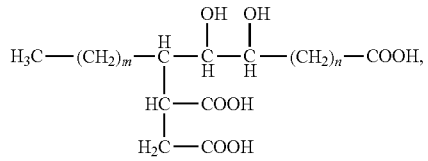

(VI)

and a combination thereof.

In formulas (V) and (VI), m and n are as disclosed above. In one advantageous embodiment, m and n are independently 0 to 10, with the proviso that m+n is less than or equal to 16.

It is to be understood that as used herein, the compound having the formula (VI) also includes the structural isomer having the formula (VIa):

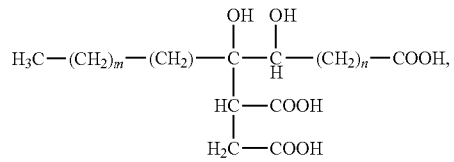

(VIa)

wherein m an n are as disclosed above.

As disclosed above, the hydroxylated carboxylic acids of formulas (I)-(VI) also include esters, salts, and anhydrides thereof, as well as combinations comprising at least one of the foregoing.

Esters of the hydroxylated carboxylic acids include any hydroxylated carboxylic acid of formulas (I)-(VI) wherein a (COOH) group is replaced by a (COOR8). For example, in one non-limiting illustrative embodiment, replacing one or more (COOH) groups by (COOR8) in the hydroxylated carboxylic acid of formula (I) produces a hydroxylated carboxylic acid ester of formula (VII):

$$(OH)_x(R^1)(COOH)_{y-p}(COOR^8)_p \quad (VII),$$

wherein $R^1$, x, and y are as disclosed above, and p is 1 to 9, more specifically 1 to 7, more specifically 1 to 5, and even more specifically 1 to 3, with the proviso that p is less than or equal to y. Similarly, replacing one or more (COOH) groups by $(COOR^8)$ groups can be done in any of the hydroxylated carboxylic acids of formulas (II)-(VI). There is no limit as to how many (COOH) groups can be replaced by $(COOR^8)$ groups in the hydroxylated carboxylic acids of formulas (I)-(VI).

The R8 group in (COOR8) is a C1-50 hydrocarbyl group. Hydrocarbyl groups include substituted or unsubstituted monovalent groups comprising carbon and hydrogen, and can be aliphatic, aromatic, or a combination of aliphatic and aromatic. Hydrocarbyl groups can also include one or more heteroatoms, such as oxygen, nitrogen, sulfur, and the like, wherein the heteroatom can be present as a substituent, e.g., a heteroatom-containing group such as halo, oxo, heterocyclo, alkoxy, hydroxy, aryloxy, —NO2, carboxy, acyl, amino, alkylamino, amino, or the like. The heteroatom can also be present as an essential structural component of the group, for example in the form of an ester or ether linkage. A hydrocarbyl group can be linear, branched, or cyclic, including polycyclic, or a combination comprising at least one of the foregoing.

In one advantageous embodiment, R8 has the formula (VIII):

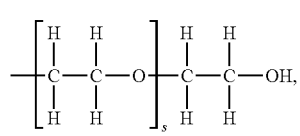
(VIII)

wherein s is 0 to 10, specifically 0 to 8, more specifically 0 to 6, and even more specifically 0 to 4.

Salts of the hydroxylated carboxylic acids include any hydroxylated carboxylic acid of formulas (I)-(VI) wherein the hydrogen atom H in a (COOH) group, an (OH) group, or a combination thereof, is replaced by M. For example, in one non-limiting illustrative embodiment, replacing one or more (COOH) and/or (OH) group by (COOM) and/or (OM) in the hydroxylated carboxylic acid of formula (I) produces a hydroxylated carboxylic acid salt of formula (IX):

(IX), wherein $R^1$, p, x, and y are as disclosed above, and q is 1 to 9, more specifically 1 to 7, more specifically 1 to 5, and even more specifically 1 to 3, with the proviso that q is less than or equal to x. Similarly, replacing one ore more (COOH) and/or (OH) groups by (COOM) and/or (OM) groups can be done in any of the hydroxylated carboxylic acids of formulas (II)-(VI). There is no limit as to how many (COOH) groups and/or (OH) groups can be replaced by (COOM) groups and/or (OM) groups in the hydroxylated carboxylic acids of formulas (I)-(VI).

In one advantageous embodiment, salts of the hydroxylated carboxylic acids include any hydroxylated carboxylic acid of formulas (I)-(VI), wherein only hydrogen atoms H in a (COOH) group are replaced by M.

M can be any cation capable of forming a salt with the hydroxylated carboxylic acids, including organic and inorganic cations. Non-limiting examples include alkali metal cations, alkaline earth metal cations, transition metal cations, ammonium cations, phosphonium cations, pyridinium cations, imidazolinium cations, pyrazolinium cations, triazolinium cations, tetrazolinium cations, and the like, as well as combinations comprising at least one of the foregoing. In one advantageous embodiment, M is selected from the group consisting of alkali metal cations, alkaline earth metal cations, ammonium cations, and a combination thereof.

Anhydrides of the hydroxylated carboxylic acids include any hydroxylated carboxylic acid of formulas (I)-(VI) wherein a pair of (COOH) groups is replaced by an anhydride functionality by a loss of one H2O molecule. For example, in one non-limiting illustrative embodiment, replacing one or more pairs of (COOH) groups by anhydride functionalities in the hydroxylated carboxylic acid of formula (I) produces a hydroxylated carboxylic acid anhydride of formula (X):

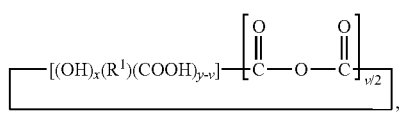
(X)

wherein $R^1$, x, and y are as disclosed above, and v is 2, 4, 6, 8, or 10, with the proviso that v is less than or equal to y. Similarly, replacing a pair (COOH) groups by an anhydride functionality can be done in any of the hydroxylated carboxylic acids of formulas (II)-(VI). There is no limit as to how many pairs of (COOH) groups can be replaced by anhydride functionalities in the hydroxylated carboxylic acids of formulas (I)-(VI).

In one advantageous embodiment, the anhydride of the hydroxylated carboxylic acids is of the formula (XI):

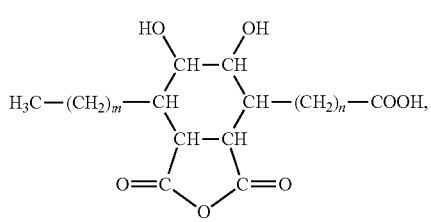
(XI)

wherein m and n are as disclosed above.

In one advantageous embodiment, the hydroxylated carboxylic acids for use herein include the products of hydroxylation of the double bond of compounds having the formula (XII)-(XIII):

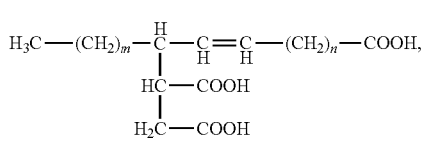
(XII)

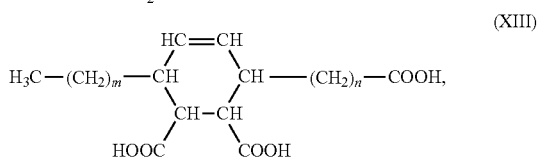
(XIII)

as well as esters thereof, salts thereof, anhydrides thereof, and combinations thereof, wherein m and n are as disclosed above.

It is to be understood that as used herein, the compounds having the formula (XII) also include compounds having the formula (XIIa):

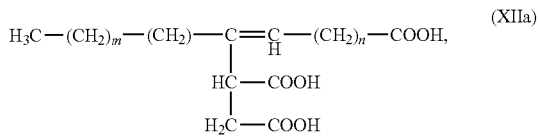
(XIIa)

wherein m and n are as disclosed above.

Non-limiting examples of compounds having the formula (XII) can be prepared by heating a fatty acid having the formula (XX):

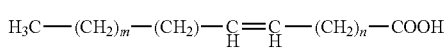

(XX)

with maleic anhydride to produce a compound having the formula (XXI):

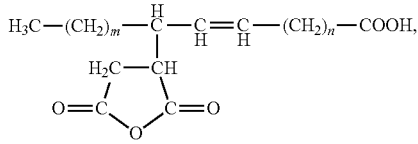

(XXI)

or a compound having the formula (XXIa):

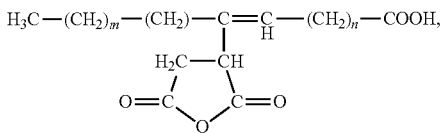

(XXIa)

wherein m and n are as disclosed above.

Heating can be effected at a temperature of about 50° C. to about 300° C., more specifically at a temperature of about 100° C. to about 250° C., and even more specifically at a temperature of about 150° C. to about 225° C. In one exemplary embodiment, heating is effected at a temperature of about 200° C. Heating can be effected for a sufficient time to allow the reaction to go to completion, which can be easily determined by one with ordinary skill in the art. In general, heating can be effected for about 1 hour to about 24 hours, more specifically about 2 hours to about 15 hours, and even more specifically about 3 hours to about 10 hours. In one exemplary embodiment, heating is effected for about 6 hours.

The compound having the formula (XXI) can be converted to an acid by hydrolysis. Hydrolysis can be effected using any of several methods available to one with ordinary skill in the art. In one embodiment, hydrolysis is effected by mixing water with the compound having the formula (XXI), and, optionally, heating for a time effective to produce the compound having the formula (XII).

Non-limiting specific examples of compounds having the formula (XII) include the compound having the formula (XXII):

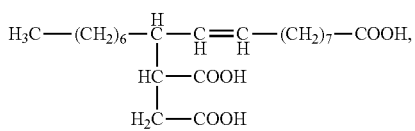

(XXII)

prepared by using oleic acid as the compound having the formula (XX) according to the above disclosed method, and the compound having the formula (XXIII):

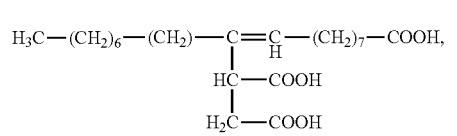

(XXIII)

prepared by using elaidic acid as the compound having the formula (XX) according to the above disclosed method. Other non-limiting examples of monounsaturated acids which can be used to prepare compounds having formula (XII) include myristoleic acid, palmitoleic acid, erucic acid.

Compounds having the formula (XIII) include tall oil fatty acids, esters thereof, salts thereof, anhydrides thereof, and combinations thereof, such as those described in U.S. Pat. Nos. 4,927,669; 5,292,480 and 6,391,257.

Non-limiting examples of compounds having the formula (XIII) include maleated tall oil fatty acids and their salts, such as TENAX 2010, reaction products of maleated tall oil fatty acids, diethylene glycol ester and their salts such as TENAX WS-5520 and WS-5560, reaction products of maleated tall oil fatty acids, ethylene glycol ester and their salts such as OCD 447 and WS-3520, and maleated tall oil such as TENAX 2015, available from MeadWestvaco, Charleston, S.C., USA.

Non-limiting examples of compounds having the formula (XIII) can be prepared by reacting a fatty acid comprising a conjugated double bond with maleic anhydride, followed by hydrolysis as disclosed above. Heating the fatty acid comprising a conjugated double bond with maleic anhydride can be effected at the above temperatures, however, in one exemplary embodiment, it is effected at a temperature of about 100° C. to about 150° C., and more specifically at about 120° C.

Non-limiting examples of fatty acids comprising a conjugated double bond include linoleic acid, alpha-linolenic acid, arachidonic acid, catalpic acid, punicic acid, rumelenic acid, alpha-parinaric acid, beta-parinaric acid, bosseopentaenoic acid, teicosapentaenoic acid, docosahexaaenoic acid, rumenic acid, jacaric acid, calendic acid, beta-eleostearic acid and α-eleostearic acid.

The compounds having the formulas (XII) and (XIII) can be converted to the compounds having the formulas (V) and (VI) using several methods available to one with ordinary skill in the art, such as, but not limited to, hydroxylation of the double bond. Hydroxylation of the double bond can be effected using any suitable method such as, but not limited to, oxidation in the presence of peroxides, osmium tetroxides, and the like. Some non-limiting methods used to hydroxylate the double bond include those described in U.S. Pat. No. 3,169,139, Japan Patent No. JP6228184, and Patent Nos. GB776757 and GB769200.

In one advantageous embodiment, unsaturated fatty acids obtained from natural sources, such as from glyceride oils, are used in the synthesis of compounds (V)-(VI), due to their renewable nature. Non-limiting examples of renewable natural sources from which unsaturated fatty acids are obtained include arachis, cashew nut, castor, chia, corn, cotton seed, hemp, linseed, lumbang, niger seed, rapeseed (canola), soybean seed, oil-palm fruit, oiticica, perilla, poppy, po-yok, rubber seed, safflower, soya, stillingia, sunflower, tobacco seed, tung, walnut, and the like.

The hydroxylated carboxylic acid further includes those that are produced from unsaturated fatty acids that are substituted. Non-limiting examples of substituted unsaturated fatty acids include vernolic acid, ricinoleic acid, and the like.

The hydroxylated carboxylic acid further includes those that are produced from polyunsaturated acid. Non-limiting examples of polyunsaturated acids include pinolenic acid and podocarbic acid.

The hydroxylated carboxylic acid can be present in the heat transfer fluid in an amount of about 0.01 percent by weight (wt. %) to about 10 wt. %, based on the total weight of the heat transfer fluid. Specifically, the hydroxylated carboxylic acid can be present in the heat transfer fluid in an amount of about 0.1 wt. % to about 5 wt. %, more specifically about 0.5 wt. % to about 4 wt. %, and even more specifically about 1 wt. % to about 3 wt. %, based on the total weight of the heat transfer fluid.

The heat transfer fluid can further comprise an alcohol, water, or a combination of an alcohol and water. It is advantageous to use deionized water, demineralized water, or deionized and demineralized water, which generally exhibit a conductivity lower than that of water which has not been deionized or demineralized. The heat transfer fluid can be a concentrated heat transfer fluid, that is, a heat transfer fluid essentially free of water, that is, comprises about 0 wt. % water, based on the total weight of the heat transfer fluid. Concentrated heat transfer fluids are advantageous for storage and shipping. Concentrated heat transfer fluids can, if desired, be combined with water prior to use. The heat transfer fluid can, on the other hand, be a diluted heat transfer fluid, that is, a heat transfer fluid comprising alcohols and water. Both concentrated and diluted heat transfer fluids can be used herein. In one embodiment, the heat transfer fluid is a concentrated heat transfer fluid. In another embodiment, the heat transfer fluid is a diluted heat transfer fluid.

Water can be present in the heal transfer fluid in an amount up to 90 wt. %, based on the total weight of the heat transfer fluid. Specifically, water can be present in the heat transfer fluid in an amount of about 0.1 wt. % to about 90 wt. %, more specifically 0.5 wt. % to about 70 wt. %, and more specifically about 1 wt. % to about 60 wt. %, based on the total weight of the heat transfer fluid. In one advantageous embodiment, water is present in an amount of about 1 wt. % to about 40 wt. %, based on the total weight of the heat transfer fluid. In another advantageous embodiment, the heat transfer fluid is essentially free of water.

The alcohol can be any alcohol available to one with ordinary skill in the art, and more specifically, any alcohol that can be used as a freezing point depressant by one with ordinary skill in the art. In one embodiment, the alcohol comprises monohydric alcohols, polyhydric alcohols, or combinations thereof.

Non-limiting examples of monohydric alcohols include methanol, ethanol, propanol, butanol, furfurol, tetrahydrofurfurol, ethoxylated furfurol, alkoxy alkanols such as methoxyethanol, and the like, and combinations thereof. Non-limiting examples of polyhydric alcohols include, ethylene glycol, diethylene glycol, triethylene glycol, propylene glycol, 1,2-propylene glycol, 1,3-propylene glycol, dipropylene glycol, butylene glycol, glycerol, glycerol-1,2-dimethyl ether, glycerol-1,3-dimethyl ether, monoethylether of glycerol, sorbitol, 1,2,6-hexanetriol, trimethylol propane, and the like, and combinations thereof.

In one embodiment, the alcohol comprises methanol, ethanol, propanol, butanol, furfurol, tetrahydrofurfurol, ethoxylated furfurol, methoxyethanol, ethylene glycol, diethylene glycol, triethylene glycol, 1,2-propylene glycol, 1,3-propylene glycol, dipropylene glycol, butylene glycol, glycerol, glycerol-1,2-dimethyl ether, glycerol-1,3 dimethyl ether, monoethylether of glycerol, sorbitol, 1,2,6-hexanetriol, trimethylol propane, or a combination thereof.

In one embodiment, the alcohol comprises ethylene glycol. In another embodiment, the alcohol comprises 1,3-propylene glycol. In yet another embodiment, the alcohol comprises ethylene glycol and 1,3-propylene glycol.

There is no limit to the amount of alcohol that can be present in the heat transfer fluid, and it can be readily determined by one with ordinary skill in the art based on the operating temperature, the ambient temperature, and the like. In general, the alcohol can be present in an amount of about 0.1 wt. % to about 99.9 wt. %, based on the total weight of the heat transfer fluid. Specifically, the alcohol can be present in the heat transfer fluid in an amount of about 1 wt. % to about 99 wt. %, more specifically about 10 wt. % to about 97 wt. %, more specifically about 15 wt. % to about 95 wt. %, more specifically about 20 wt. % to about 90 wt. %, more specifically about 25 wt. % to about 85 wt. %, more specifically about 30 wt. % to about 80 wt. %, more specifically about 40 wt. % to about 70 wt. %, and even more specifically about 50 wt. % to about 60 wt. %, based on the total weight of the heat transfer fluid. In one advantageous embodiment, the alcohol is present in amount of 40 wt. % to about 99 wt. %, based on the total weight of the heat transfer fluid.

The heat transfer fluid can further include corrosion inhibitors. There is no particular limitation to the corrosion inhibitors for use herein, and they can comprise azoles, siloxanes, colloidal silica, silicates, carboxylates, tall oil fatty acids, borates, nitrates, nitrites, alkali or alkaline earth metal, ammonium or amine salts thereof, or the like, or a combination thereof.

The amount of corrosion inhibitors can be readily determined by one with ordinary skill in the art, depending on the application and on the corrosion inhibitor. In general, the corrosion inhibitors are present in an amount of about 0.01 wt. % to about 10 wt. %, specifically about 0.1 wt. % to about 8 wt. %, more specifically about 0.5 wt. % to about 4 wt. %, based on the total weight of the heat transfer fluid.

Azoles include five-membered heterocyclic compounds having 1 to 4 nitrogen atoms as part of the heterocycle. Non-limiting examples of azole-based corrosion inhibitors include pyrroles, pyrazoles, imidazoles, triazoles, thiazoles and tetrazoles according to formulas (XIV)-(XVII):

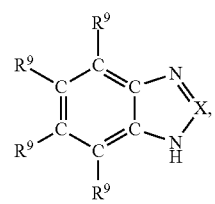

(XIV)

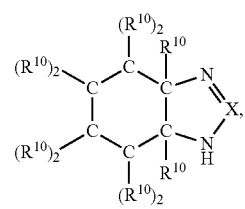

(XV)

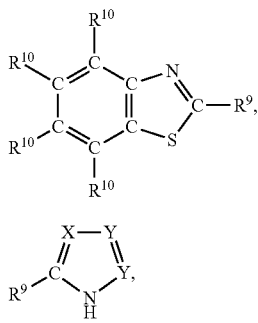

(XVI)

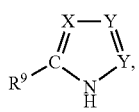

(XVII)

and combinations thereof, wherein $R^9$ is independently a hydrogen atom, SH, $SR^{11}$, or a $C_{1-20}$ alkyl group, wherein $R^{11}$ is a $C_{1-20}$ alkyl group group, $R^{10}$ is independently a hydrogen atom, a halogen atom such as Cl or Br, or a $C_{1-20}$ alkyl group, X is independently N, CSH, $CSR^{11}$, CH, or $CR^{11}$; and Y is independently N, $CR^{11}$ or CH.

Non-limiting examples of azoles include pyrrole, methylpyrrole, pyrazole, dimethyl pyrazole, benzotriazole, tolyltriazole, methyl benzotriazole such as 4-methyl benzotriazole and 5-methyl benzotriazole, butyl benzotriazole, mercaptobenzothiazole, benzimidazole, halo-benzotriazole such as chloro-methylbenzotriazole, tetrazole, methyl tetrazole, mercapto tetrazole, thiazole, 2-mercaptobenzothiazole and the like. In one embodiment, the azole compound comprises benzotriazole, tolyltriazole, mercaptobenzothiazole, or a combination thereof. In one exemplary embodiment, the azole-based corrosion inhibitor is selected from benzotriazole, tolyltriazole, or a combination thereof.

The azoles can be present in the heat transfer fluid in an amount up to about 10 wt. %, specifically about 0.01 wt. % to about 8 wt. %, more specifically about 0.05 wt. % to about 4 wt. %, based on the total weight of the heat transfer fluid.

Colloidal silica comprises any colloidal silica that can be used as a corrosion inhibitor in heat transfer fluids. Non-limiting examples include colloidal silica of an average particle size of about 1 nanometer (nm) to about 200 nm, more specifically from about 1 nm to about 100 nm, and even more specifically from about 1 nm to about 40 nm. The colloidal silica is advantageous as a corrosion inhibitor, and can advantageously improve the heat transfer properties of the heat transfer fluid. While not wishing to be bound by theory, it is believed that the use of silica of a particular average particle size provides improvements in heat transfer efficiency and/or heat capacity by providing a larger surface area for contact with the heat transfer fluid.

Non-limiting examples of colloidal silica include LUDOX from DuPont or Grace Davidson, NYACOL or BINDZIL from Akzo Nobel or Eka Chemicals, SNOWTEX from Nissan Chemical. Other suppliers of colloidal silica include Nalco and the like.

The colloidal silica can be present in the heat transfer fluid in an amount of up to about 10,000 parts per million by weight (ppm) in equivalent Si concentration, more specifically of about 1 ppm to about 2000 ppm, and even more specifically about 10 ppm to about 600 ppm, based on the total weight of the heat transfer fluid.

Siloxanes include polysiloxanes and organosilane compounds comprising a silicon-carbon bond. In one embodiment, the polysiloxanes include those having the formula (XVIII):

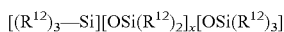

(XVIII), wherein $R^{12}$ is independently an alkyl group or a $C_{1-200}$ polyalkylene oxide copolymer, and x is from 0 to 100. In one exemplary embodiment, $R^{12}$ comprises a polyalkylene oxide copolymer comprising $C_{2-6}$ alkylene oxide units, and more specifically $C_{2-4}$ alkylene oxide units. Polysiloxanes having a similar general structure but are outside the scope of formula (XVIII), including commercially available polysiloxanes for which the structure is unknown, can also be used.

Non-limiting examples of commercially available polysiloxanes include the SILWET siloxanes from GE Silicones/OSi Specialties, and other similar siloxane-polyether copolymers available from Dow Corning or other suppliers. In one exemplary embodiment, siloxane-based corrosion inhibitors include SILWET L-77, SILWET L-7657, SILWET L-7650, SILWET L-7600, SILWET L-7200, SILWET L-7210 and the like.

Organosilane compounds are those that include a silicon-carbon bond capable of hydrolyzing in the presence of water to form a silanol, that is, a compound comprising silicon hydroxide. Organosilane compounds comprise those of the formula (XIX):

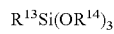

(XIX), wherein $R^{13}$ and $R^{14}$ are independently a $C_{1-30}$ aliphatic (including cycloaliphatic) group or aromatic group. In one embodiment, $R^{13}$ is selected from $C_{1-20}$ alkyl groups (including cycloalkyl groups), alkoxy groups, and alkylene groups, and can comprise a heteroatom such as N, S, or the like, in the form of functional groups such as amino groups, epoxy groups, or the like, and $R^{14}$ is independently selected from $C_{1-6}$ alkyl groups. Organosilane compounds for which the structure is unknown or which is outside the scope of this formula can also be suitable for use as siloxane-based corrosion inhibitors.

Non-limiting examples of commercially available organosilane compounds include the SILQUEST and FORMASIL surfactants from GE Silicones/OSi Specialties, and other suppliers. In an exemplary embodiment, siloxane-based corrosion inhibitors comprise FORMASIL 891, FORMASIL 593, FORMASIL 433, SILQUEST Y-5560 (polyalkyleneoxidealkoxysilane), SILQIJEST A-186 (2-(3,4-epoxycyclohexyl)ethyltrimethoxysilane), SILQIJEST A-187 (3-glycidoxypropyltrimethoxysilane), or other SILQUEST organosilane compounds available from GE Silicones, Osi Specialties or other suppliers or the like.

Other non-limiting examples of organosilane compounds for use herein include 3-aminopropyltriethoxysilane, N-2-(aminoethyl)-3-aminopropyltrimethoxysilane, octyltriethoxysilane, vinyltriethoxysilane, vinyltrimethoxysilane, methyltriethoxysilane, 3-methacryloxypropyltrimethoxysilane, 3-mercaptopropyltrimethoxysilane, isobutyltrimethoxysilane, phenyltrimethoxysilane, methyltrimethoxysilane, and those organosilane compounds having a structure similar to the foregoing, but varying numbers of carbon atoms.

The siloxane-based corrosion inhibitor can be present in the heat transfer fluid in an amount up to about 10 wt. %, more specifically about 0.02 wt. % to about 2 wt. %, based on the total weight of the heat transfer fluid.

Corrosion inhibitors for use herein can also include a silicate present in an amount of from 30 ppm to 2000 ppm by weight in equivalent Si concentration, in combination with a silicate-stabilizing silicone. Non-limiting examples of silicate-stabilizing silicones include Silquest Y-5560 organosilane, sodium (trihydroxysilyl)-propylmethylphosphonate, and organic phosphosilicone compounds (i.e., O1.5Si—C3H6-P(O)(O—Na+)(OC2H5) such as those disclosed in U.S. Pat. No. 4,629,602. In one embodiment, the silicate:silicone ratio is about 20:1 to about 1:2 by weight.

The silicates include inorganic silicates and organic silicates. Inorganic silicates follow the general reduced formula SiOx and can be ionic or neutral, polymeric or non-polymeric. Non-limiting examples of inorganic silicates include SiO2, SiO44-, Si2O76-, SiO32-, and the like, and combinations thereof. The inorganic silicates can also include metal oxides that are alkaline upon dissolution in water, and which aid in the dissolution of the inorganic silicates. The weight ratio of the metal oxide to the inorganic silicate is generally from about 2:1 to about 1:5, specifically from about 1:1 to about 1:3.5. Non-limiting examples of metal oxides that are alkaline upon dissolution in water include alkali metal oxides such as Na2O and K2O, alkaline earth metal oxides such as MgO and CaO, and the like, as well as combinations thereof.

Inorganic silicates for use herein can be obtained from, for example, the Philadelphia Quartz Company, and are sold under the tradename RU SILICATE (sodium silicate, Na2O:SiO2=1:2.4) and KASIL 6 (potassium silicate, K2O:SiO2=1:2.1).

Organic silicates include silicate esters such as, but not limited to, those having the formula Si(OR15)4 wherein R15 is independently selected from the group consisting of C1-36 alkyl, aryl, alkoxyalkyl, alkoxyaryl, hydroxyalkoxy, and a combination thereof. Advantageously, a tetraalkylorthosilicate ester with C1-20 alkyl groups (e.g., tetramethylorthosilicate, tetraethylorthosilicate, and the like) can be used. The silicate ester can be present in the heat transfer fluid in an amount of up to about 5 wt. %, and advantageously about 0.01 wt. % to about 5 wt. %, based on the total weight of the heat transfer fluid.

Polymers of the silicates, silicones, or siloxanes can also be used as corrosion inhibitors. They include phosphonate-silicate, sulfonate-silicate, carboxylate-silicate and siloxane-silicate copolymers generally used in the art in silicate-containing heat transfer fluids. These copolymers can be preformed or can be formed in situ upon combination of a water-soluble silicate and a water-soluble phosphonate, sulfonate, or siloxane in an aqueous solution at ambient temperature. These copolymers are generally referred to as "siloxane-silicate" copolymers in that each contains silicon in addition to the phosphonate, sulfonate, carboxylate, etc., moiety. In one advantageous embodiment, the siloxane-silicate copolymers provide improved brazed metal corrosion inhibition over the use of simple metal silicates, since the siloxane-silicate copolymers substantially inhibit the gelation tendency of water-soluble silicates at a pH of about 7 to about 11.

Other suitable silicones (or siloxane compounds) or siloxane-silicate copolymers which can be utilized herein include, but are not limited to, those described in U.S. Pat. Nos. 3,341,469; 3,337,496; 3,312,622; 3,248,329; 3,198,820; 3,203,969; 4,093,641; 4,287,077; 4,333,843; 4,352,742; 4,354,002; 4,362,644; 4,370,255; 4,629,602; 4,701,277; and 4,772,408; and also in U.S. Patent Publication No. 2006/0017044.

Non-limiting examples of carboxylates for use herein include saturated and unsaturated aliphatic, and aromatic mono-, di- and tricarboxylic acids, and salts and isomers thereof, and any combination thereof. Specifically, the carboxylates include C4-25 mono-, di-, and tri-carboxylic acids. Non-limiting examples of the foregoing include 2-ethyl hexanoic acid, neodecanoic acid, benzoic acid, p-toluic acid, p-ethyl benzoic acid, t-butylbenzoic acid, hydroxybenzoic acid, methoxy benzoic acid, dodecanedioic, undecanedioic acid and sebacic acid, as well as esters thereof, salts thereof, anhydrides thereof, and combinations thereof. In one advantageous embodiment, the carboxylates include hydroxybenzoic acid, alkyl benzoic acid, alkoxybenzoic acid of the formula R16O(C6H4)COOH wherein R16 is a C1-C5 alkyl group, cinnamic acid, alkyl cinnamic acid, alkoxy cinnamic acid of the formula R17(C6H4)CHCOOH wherein R17 is C1-5 alkyl group or alkoxy group, or combinations thereof.

The carboxylates can be present in an amount of about 0.01 wt. % to about 10 wt. %, more specifically about 0.1 wt. % to about 8 wt. %, even more specifically about 1 wt. % to about 5 wt. %, based on the total weight of the heat transfer fluid.

In one exemplary embodiment, the corrosion inhibitor comprises about 1 wt. % to about 5 wt. % of a carboxylate selected from C6-24 aromatic and aliphatic, mono-, di- and tri-carboxylic acids, esters thereof, salts thereof, anhydrides thereof, and combinations thereof, based on the total weight of the heat transfer fluid.

In another exemplary embodiment, the corrosion inhibitor comprises about 0.05 wt. % to about 1.5 wt. % of an azole compound, and about 0.2 wt. % to about 5 wt. % of a carboxylic acid selected from C6-24 aromatic and aliphatic, mono-, di- and tri-carboxylic acids, esters thereof, salts thereof, anhydrides thereof, and combinations thereof, based on the total weight of the heat transfer fluid.

Non-limiting examples of tall oil fatty acids include those of formula (XIII) disclosed above. The tall oil fatty acids can be present in an amount of up to about 10 wt. %, more specifically about 0.02 to about 7 wt. %, based on the total weight of the heat transfer fluid.

The heat transfer fluid can further comprise oxy-anions of molybdenum, tungsten, vanadium, phosphorus, or antimony, as well as combinations thereof. In one exemplary embodiment, the oxy-anion is selected from molybdenum, phosphorous, and a combination thereof.

In general, water-soluble salts of such oxy-anions can be used. Specific examples include alkali metal, alkaline earth metal, and ammonium salts of molybdates, tungstates, metatungstates, vanadates, metavanadates, ortho phosphates, pyro-phosphates, hexametaphosphates, polyphosphates, phosphoric acid, antimony tartrates, and the like. In one embodiment, the water-soluble salts include the alkali metal salts, ammonium salts, and a combination thereof. Non-limiting examples of antimony tartrates include those of the formula E(SbO)C4H4O6 and the hydrates E(SbO)C4H4O6.wH2O, wherein E is an alkali metal cation, alkaline earth metal cation, ammonium cation, or a combination thereof, and w is the amount of hydration, and is not limited to any number, but can generally be 0-20, specifically 1-10, more specifically 1-5, and more specifically 1-3, or the like. Other salts thereof, and combinations thereof can also be used. In one embodiment alkali metal and ammonium salts are used.

Non-limiting examples of oxy-anions suitable for use herein include sodium molybdate, sodium molybdate dihydrate, sodium tungstate, and ammonium metatungstate, such as those available from North Metal & Chemical Company (York, Pa., USA), sodium molybdate and ammonium di-, hepta- or octa-molybdates such as those available from Climax Molybdenum Company (Phoenix, Ariz., USA), potassium or sodium vanadates or metavanadates, sodium molybdate, ammonium metatungstate and ammonium paratungstate such as those available from Alcan Chemicals (Stamford, Conn., USA, a division of Rio Tinto Alcan), potassium or sodium phosphates, such as monosodium or monopotassium phosphate, disodium or dipotassium phosphate, trisodium or tripotassium phosphate, tetrasodium or tetrapotassium pyrophosphate, sodium pyrophosphate, sodium or potassium tripolyphosphate, potassium polyphosphate, sodium hexametaphosphate, and phosphoric acid, polyphosphoric acid, and other phosphates, such as alkali earth phosphates and ammonium phosphates such as those available from Innophos, Inc. (Cranbury, N.J., USA) or ICL Performance Products LP (St. Louis, Mo., USA) and other suppliers, and potassium antimony tartrates (potassium antimonyl tartrates), potassium antimonite, and potassium hexahydroxyantimonate such as those available from Sigma-Aldrich (St. Louis, Mo., USA) or LabChem, Inc. (Pittsburgh, Pa., USA). Similar oxy-anion products from other suppliers can also be used.

The oxy-anion of molybdenum, tungsten, vanadium, phosphorus, antimony, or a combination thereof can be present in an amount of about 0.01 wt. % to about 10 wt. %, specifically about 0.05 wt. % to about 8 wt. %, and even more specifically about 0.1 wt. % to about 5 wt. %, based on the total weight of the heat transfer fluid.

In one advantageous embodiment, a combination of an oxy-anion of phosphorus with an oxy-anion selected from an oxy-anion of molybdenum, tungsten, vanadium, antimony and a combination thereof, can be used. A synergistic effect is thus observed between the oxy-anion of phosphorus and the oxy-anion selected from the oxy-anion of molybdenum, tungsten, vanadium, and antimony. The oxy-anion of phosphorus can be used in an amount of about 0.01 wt. % to about 3 wt. %, specifically about 0.1 wt. % to about 2 wt. %, and more specifically about 0.2 wt. % to about 1 wt. %, based on the total weight of the heat transfer fluid, and the combination of oxy-anions of molybdenum, tungsten, vanadium, and antimony can also be used in an amount of about 0.01 wt. % to about 3 wt. %, specifically about 0.1 wt. % to about 2 wt. %, and more specifically about 0.2 wt. % to about 1 wt. %, based on the total weight of the heat transfer fluid.

The heat transfer fluids can also comprise additional additives such as colorants, antifoam agents, wetting agents, biocides, pH adjusting agents, buffering agents, bitterants, dispersants, or any other common ingredient that is used in heat transfer fluids by those with ordinary skill in the art, or combinations thereof, in amounts of up to 10 wt. %, based on the total weight of the heat transfer fluid, as long as they do not adversely affect the heat transfer fluid.

The heat transfer fluid can be prepared by mixing the components together and homogenizing the resulting mixture. This can be effected using any suitable method available to one with ordinary skill in the art. Generally, the alcohol and water are advantageously mixed together first. The other components and additives are then added to the alcohol-water mixture by mixing and adequate stirring. However, any order of addition can be used.

In one embodiment, the above disclosed heat transfer fluid can be used as an additive package for use with heat transfer fluids. That is, an additive package comprising a hydroxylated carboxylic acid of formula (I) can be used to treat another heat transfer fluid that comprises water and/or alcohols. The other heat transfer fluid can be any heat transfer fluid that would benefit from the hydroxylated carboxylic acid of formula (I).

Thus, one embodiment is a method of treating a heat transfer fluid, comprising mixing with the heat transfer fluid an additive package comprising a hydroxylated carboxylic acid of formula (I). The heat transfer fluid comprises water and/or alcohols.

In one embodiment, the additive package is free of water and/or alcohols. In this embodiment, the additive package comprises any of the components disclosed above (except water and/or alcohols), in addition to the hydroxylated carboxylic acid of formula (I). The components can be used in any suitable amount so that in the final mixture, the amounts are those described above.

The amount of the components can be easily determined by one with ordinary skill in the art. For example, if the additive package is to be used in a heat transfer system comprising a total of 2000 grams of heat transfer fluid composition, and if the desired amount of the hydroxylated carboxylic acid of formula (I) is about 0.01 to about 10 wt. %, based on the total weight of the heat transfer fluid, then the desired amount of the hydroxylated carboxylic acid of formula (I) can be calculated as (amount of hydroxylated carboxylic acid)/(amount of hydroxylated carboxylic acid+2000 grams)×100=about 0.01 to about 10, resulting in the amount of hydroxylated carboxylic acid of formula (I) in a total of 2000 grams of heat transfer fluid composition being about 0.22 to about 222 grams.

In general, the hydroxylated carboxylic acid of formula (I) can be present in the additive package in an amount of about 1 wt. % to about 100 wt. %, specifically about 10 wt. % to about 90 wt. %, more specifically about 20 wt. % to about 80 wt. %, more specifically about 30 wt. % to about 70 wt. %, and even more specifically about 40 wt. % to about 60 wt. %, based on the total weight of the additive package. In one advantageous embodiment, the oxy-anion is present in an amount of about 20 wt. % to about 60 wt. %, based on the total weight of the additive package.

The corrosion inhibitors can be present in the additive package in an amount of about 1 wt. % to about 99 wt. %, specifically about 10 wt. % to about 90 wt. %, more specifically about 20 wt. % to about 80 wt. %, more specifically about 30 wt. % to about 70 wt. %, and even more specifically about 40 wt. % to about 60 wt. %, based on the total weight of the additive package. In one advantageous embodiment, the corrosion inhibitors are present in an amount of about 40 wt. % to about 80 wt. %, based on the total weight of the additive package.

The additional additives generally used in heat transfer fluids such as the above disclosed colorants, antifoam agents, wetting agents, biocides, bitterants, dispersants or combinations thereof, can be used in the additive package in amounts of up to 50 wt. %, based on the total weight of the additive package.

The additive package can be used in any suitable form, such as solid, powder, gel, capsule, and the like, and can be an immediate release package or an extended release package.

In one advantageous embodiment, the additive package is used as a concentrated additive solution. The solvent for the concentrated additive solution can be any suitable solvent. Advantageously, the solvent can be any of the above described water and/or alcohols. For example, the additive package can be used as a concentrated solution of water, ethylene glycol, diethylene glycol, 1,2-propylene glycol, 1,3-propylene glycol, glycerol or a combination thereof.

When used as a concentrated additive solution, the solvent can be present in an amount of about 0.5 to about 50 percent by weight, based on the total weight of the additive package. More specifically, the solvent can be present in an amount of about 1 wt. % to about 40 wt. %, more specifically about 2 wt. % to about 30 wt. %, and even more specifically about 3 wt. % to about 20 wt. %, based on the total weight of the additive package.

In one embodiment, a heat transfer system comprises the heat transfer fluid and/or additive package disclosed above. The heat transfer system comprises an aluminum component, a magnesium component, or a combination thereof. The heat transfer fluid is in fluid communication with the aluminum component and/or the magnesium component. The heat transfer fluid is effective at reducing and/or eliminating corrosion due to cavitation, erosion, cavitation-erosion, brazing, galvanic, pitting, crevice corrosion, and/or residual fluxes used in brazing processes, and/or the like.

As used herein, "aluminum" refers to aluminum metal, alloys thereof, or a combination thereof, and "magnesium" refers to magnesium metal, alloys thereof, or a combination thereof.

An "aluminum component", as used herein, refers to a component of the heat transfer system that comprises aluminum and/or an aluminum alloy. The component comprises a single aluminum component, or several components comprising at least one aluminum component joined together. The components can be joined together using brazing. In one embodiment, brazing is effected using controlled atmosphere brazing (CAB) in the presence of a fluxing agent comprising halide anions. In another embodiment, the fluxing agent comprises fluoride and chloride anions. In one advantageous embodiment, the fluxing agent comprises fluoride anions.

As used herein, a "magnesium component" refers to a component of the heat transfer system that comprises magnesium and/or a magnesium alloy. The component comprises a single magnesium component, or several components comprising at least one magnesium component joined together. The components can be joined together using brazing. In one embodiment, brazing is effected using controlled atmosphere brazing (CAB) in the presence of a fluxing agent comprising halide anions. In another embodiment, the fluxing agent comprises fluoride and chloride anions. In one advantageous embodiment, the fluxing agent comprises fluoride anions The heat transfer system can be any assembly comprising aluminum and/or magnesium components. The assemblies can comprise internal combustion engines and alternative power sources. Non-limiting examples of alternative power sources include batteries, fuel cells, solar cells or solar panels, photovoltaic cells, and internal combustion engines powered by the condensation of steam, natural gas, diesel, hydrogen, and/or the like. In one embodiment, alternative power sources include devices powered by internal combustion engines operating with a clean heat transfer system, that is, a heat transfer system that does not contribute to the concentration of ionic species in the heat transfer fluid. Such alternative power sources can be used alone or in combination, such as those employed in hybrid vehicles.

Assemblies comprising such alternative power sources include any article that can traditionally be powered by an internal combustion engine, such as automotive vehicles, boats, generators, lights, aircrafts and airplanes, trains or locomotives, military transport vehicles, stationary engines, and the like. The assemblies also include additional systems or devices required for the proper utilization of alternative power sources, such as electric motors, DC/DC converters, DC/AC inverters, electric generators, and other power electronic devices, and the like. The assemblies can also include systems or devices required for the proper utilization of the alternative power sources such as electric motors, DC/DC converters, DC/AC inverters, electric generators, and other power electronics and electrical devices, and the like.

The disclosed assemblies comprise a power source comprising a heat transfer system in thermal communication with the alternative power source and with the heat transfer fluid. In one embodiment, the heat transfer system comprises a circulation loop defining a flow path for the heat transfer fluid.

In an exemplary embodiment referred to in FIG. 1, the power source is an internal combustion engine, and the heat transfer system comprises aluminum and/or magnesium components. It will be understood that while FIG. 1 refers to an exemplary embodiment wherein the heat transfer system comprises aluminum and/or magnesium components, it can further comprise other metals or alloys such as copper, carbon steel, brass, or the like. A combination of the metals or alloys can also be used.

Thus, referring now to FIG. 1, an exemplary heat transfer system 10 comprises a heat transfer fluid reservoir 12, a pump 14, an engine 16, a heater core 18, a thermostat 20, a radiator cap 22, a radiator 24 and an overflow tank 26. The heat transfer system can further comprise conduits such as pipe 30, valves (not shown), sensors (not shown), pumps and other components. Each of the components of the heat transfer system 10 can comprise aluminum and/or magnesium components. In one exemplary embodiment, at least one of the components of the heat transfer system 10 comprises aluminum and/or magnesium components. In another exemplary embodiment, each of the pump 14, the engine 16, the heater core 18, the thermostat 20, the radiator cap 22, the radiator 24, and the overflow tank 26 comprise aluminum and/or magnesium components. In another exemplary embodiment, one or more components comprise aluminum and/or magnesium components while one or more other components do not comprise aluminum and/or magnesium components.

The reservoir 12 maintains the heat transfer fluid in an environment free from undesirable contaminants when the fluid is not circulating. In one embodiment, reservoir 12 comprises plastic.

The pump 14 drives the fluid through the heat transfer system 10. Specifically, pump 14 routes fluid from the reservoir, through an engine block of the engine 16, that is, through a first set of interior passages of the engine that are disposed proximate the engine cylinder, through heater core 18, through a second set of interior passages of the engine block, and to the thermostat 20. Depending on the position of the thermostat 20, the fluid is then routed through either the radiator cap 22, the radiator 24, then to the pump 14, or directly to the pump 14. The pump 14 can be a centrifugal pump driven by a belt connected to a crankshaft of the engine 16. The pump 14 pumps heat transfer fluid through the heat transfer system 10 when the engine 16 is operating. The pump 14 can comprise a rotating component comprising an impeller and a shaft. The pump 14 can further comprise a stationary component comprising a casing, a casing cover, and bearings. In an exemplary embodiment both the rotating component of the pump and the casing component of the pump comprise aluminum and/or magnesium components. In another exemplary embodiments only the rotating component, the casing component, or subcomponents of the rotating component and casing component comprise aluminum and/or magnesium components.

The engine 16 comprises the engine block, cylinders, cylinder connecting rods, and a crankshaft. The engine block comprises internal passageways disposed therethrough. The internal passageway can be cast or machined in the engine block. The heat transfer fluid can be routed through the internal passageways of the engine to transfer heat from the engine. These passageways direct the heat transfer so that the fluid can transfer heat away from the engine to optimize engine performance.

In an exemplary embodiment the metal engine components comprise aluminum and/or magnesium components. Specifically, the engine block, the cylinders, the cylinder connecting rods, and the crankshaft comprise aluminum and/or magnesium components. In another exemplary embodiment, certain engine components comprise aluminum and/or magnesium components, while other engine components do not comprise aluminum and/or magnesium components. For example, the engine block can comprise aluminum and/or magnesium components, while the cylinder, cylinder connecting rods, and the crankshaft can comprise steel.

The heater core 18 cools the heat transfer fluid while heating the vehicle interior. The heater core 18 comprises a series of thin flattened tubes having a high interior surface area and exterior surface area such that heat can be effectively transferred away from the heat transfer fluid. In an exemplary embodiment, the heater core 18 comprises aluminum and/or magnesium components, such as tubes. In another exemplary embodiment the heating core comprises tubes joined together by other joining methods or the heating core can be cast as a single unit. Air can be forced past the heater core to increase the cooling rate of the heat transfer fluid.

The thermostat 20 measures the temperature indicative of the heat transfer fluid temperature and selectively routes the heat transfer fluid to the radiator or to the pump. Thermostat 20 routes the heat transfer fluid to the radiator when the temperature of the heat transfer fluid is greater than or equal to the selected temperature and to the pump when the temperature of the heat transfer fluid is less than the selected temperature. The thermostat has an inlet portion, a radiator outlet portion, a radiator bypass outlet portion, and a valve portion. A single housing member can define the inlet portion, the radiator outlet portion, and the radiator bypass outlet portion. The valve portion is disposed within the single housing member and provides selective communication between the inlet portion and both the radiator outlet portion and the radiator bypass outlet portion. When the valve is in a closed position, the thermostat routes the heat transfer fluid directly to the pump. When the valve is in the open position, the thermostat routes the heat transfer fluid through the radiator. In an exemplary embodiment, the thermostat valve portion and the thermostat housing member comprise aluminum and/or magnesium components. In another exemplary embodiment, only the housing or only the valve portion comprises aluminum and/or magnesium components.

The radiator cap 22 seals the heat transfer system and maintains the heat transfer fluid at a selected pressure to prevent the heat transfer fluid from boiling. In an exemplary embodiment, the radiator cap 22 comprises aluminum and/or magnesium components.

The radiator 24 cools the heat transfer fluid. The radiator 24 can comprise a series of thin flattened tubes having a high interior surface area and exterior surface area such that heat can be effectively transferred from the heat transfer fluid. In an exemplary embodiment, the radiator 24 comprises aluminum and/or magnesium components, such as tubes. In another exemplary embodiment the radiator can comprise tubes joined together by other joining methods or case as a single unit. Air can be forced past the radiator to increasing the cooling rate of the heat transfer fluid.

Figure 2:
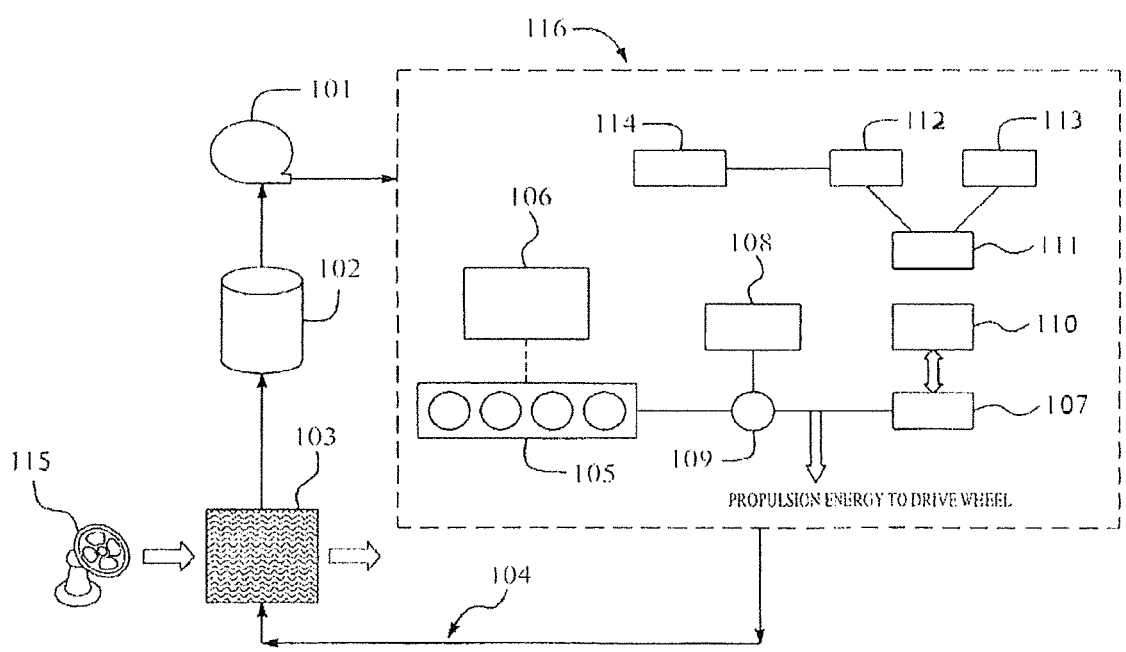
FIG. 2 is a schematic diagram of another exemplary heat transfer system.

In another exemplary embodiment referred to in FIG. 2, an assembly comprises a power source which can be an internal combustion engine, or advantageously, an alternative power source, specifically a solar cell or fuel cell. The heat transfer system comprises aluminum and/or magnesium components. The assembly can also comprise a regenerative braking system. It will be understood that while FIG. 2 refers to an exemplary embodiment wherein the heat transfer system comprises aluminum and/or magnesium components, it can also comprise any other metal or metal alloy, such as copper, carbon steel, brass, or the like. A combination of the metals or alloys can also be used.

Thus, referring now to FIG. 2, an exemplary heat transfer system 116 comprises an internal combustion engine 105, or fuel cells 105 or solar cells 105 as the primary power source 107. It also comprises a rechargeable secondary battery 112 or an optional ultra-capacitor 113 that can be charged via the assembly's regenerative braking system. The battery 112 and/or the ultra-capacitor 113 can act as secondary power sources. The assembly can further comprise power electronic devices, such as DC/DC converters 110, DC/AC inverters 110, generators 108, power splitting devices 109, and/or voltage boost converters 111, and the like. In addition, the assembly can contain fuel cell or solar cell "balance of plant" subsystems 106. These can be air compressors, pumps, power regulators, and the like. The assembly also comprises HAVC systems 114, such as, air-conditioning system for the climate control of assembly interior space. The heat transfer system 116 further comprises a pump 101, heat transfer fluid flow path 104, heat transfer fluid tank 102, and a radiator or heat exchanger 103, and a fan 115. The fan can be substituted by an external cooling source, such as a different (or isolated) cooling system with its own cooling media.

In one embodiment, the alternative power source is a fuel cell. The fuel cell is in thermal communication with the heat transfer systems and fluids. The fuel cell comprises aluminum and/or magnesium components.

The heat transfer fluid can be used in a number of different types of fuel cells comprising an electrode assembly comprising an anode, a cathode, and an electrolyte, and a heat transfer fluid in thermal communication with the electrode assembly or fuel cell. In one embodiment the heat transfer fluid can be contained or flow in channel or flow path defined by a circulation loop or heat transfer fluid flow channel in thermal communication with the fuel cell.

Non-limiting examples of fuel cells include PEM (Proton Exchange Membrane or Polymer Electrolyte Membrane) fuel cells, AFC (alkaline fuel cell), PAFC (phosphoric acid fuel cell), MCFC (molten carbonate fuel cell), SOFC (solid oxide fuel cell), and the like. In one exemplary embodiment, the heat transfer fluid is used in PEM and AFC fuel cells.

In one embodiment, a method of transferring heat comprises contacting a heat transfer system comprising aluminum and/or magnesium components, with a heat transfer fluid comprising a hydroxylated carboxylic acid of formula (I). The heat transfer fluid and the heat transfer system include any of the above disclosed, as well as combinations thereof.

The invention is further illustrated by the following non-limiting examples.

EXAMPLES

Coolant A concentrate contained 1.6 wt. % NaOH, 2.0512 wt. % sebacic acid, 0.2 wt. % sodium tolytriazole, 0.2 wt. % of a polypropylene glycol antifoam, 0.001 wt. % uranine dye, 0.5 wt. % $NaNO_3$ (40%), and 0.3 wt. % of OCD-448. Wt.% is based on the total weight of the concentrate. The balance of the concentrate was ethylene glycol.

Coolant C concentrate contains 2-3 wt. % 2-ethyl hexanoic acid, 0.5-1 wt. % neodecanoic acid, 0.2 wt. % sodium tolytriazole, 0.2 wt. % of a polypropylene glycol antifoam, and 0.4 wt. % of OCD-448. NaOH was used to adjust the pH to 8.7. The balance of the concentrate was ethylene glycol.

The coolant concentrates were diluted to make a 50 volume percent mixture using water and the mixtures were used in the following examples. Foaming was tested by adding 50 milliliters of the room temperature (20° C.) test mixture to a 100 milliliter graduated cylinder. The cylinder was covered and shaken vigorously for 30 seconds. The graduated cylinder was then placed on a level surface and allowed to stand undisturbed for 10 seconds. The foam volume was determined by reading the top level of the foam to the nearest milliliter and subtracting 50 milliliters to account for the liquid level.

OCD-448 is a maleated fatty acid which is hydroxylated by hydrogen peroxide or OH radicals generated by the reduction of oxygen on the metal coupon surfaces thereby generating the hydroxylated carboxylic acid in situ.

Example 1 used a solution consisting of 50 vol.% coolant A and 50 vol.% de-ionized water. Example 2 used a solution consisting of 50 vol.% coolant C and 50 vol.% de-ionized water. For example 3, 500 ml of a solution consisting of 50 vol.% coolant C and 50 vol. % de-ionized water was placed in a glass beaker fitted with a Teflon cap and a glass condenser. The beaker was heated at 103° C. for 2 hours while aerated by air bubbling. For example 4 the conditions of example 3 were employed except that multiple metal coupons specified by ASTM D1384 were in the beaker and the beaker was heated for 3 hours. For example 5 the conditions of example 4 were used except that the beaker was heated for five hours. Results are shown in Table 1.

TABLE 1

| Example | Foam volume |
| --- | --- |
| 1* | 25 |
| 2* | 22 |
| 3* | 21 |
| 4 | 15 |
| 5 | 12 |

As seen in the examples, the presence of a hydroxylated carboxlic acid reduces the amount of foam, reducing the amount of foam almost by half.

This written description uses figures in reference to exemplary embodiments and examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety unless otherwise indicated. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Further, it is understood that disclosing a range is specifically disclosing all ranges formed from any pair of any upper range limit and any lower range limit within this range, regardless of whether ranges are separately disclosed. It is not intended that the scope of the invention be limited to the specific values recited when defining a range.

The use of the terms "a", "an", "the", and similar referents in the context of describing the invention (especially in the context of the following claims) are to be construed to cover both the singular and the plural, unless otherwise indicated herein or clearly contradicted by context. Further, it should be noted that the terms "first", "second", and the like herein do not denote any order, quantity, or importance, but rather are used to distinguish one element from another.

The modifier "about" used in connection with a quantity is inclusive of the stated value and has the meaning dictated by the context (e.g., it includes the degree of error associated with measurement of the particular quantity).

As used herein, "comprising", "comprises", and other variants, are open terms, and therefore allow the presence of other components, but do not mandate it. Therefore, "consisting of", "consists of", and other variants are within the scope of "comprising", "comprises", and the like.

As used herein, "ammonium" includes NH4+, primary organoammonium, secondary organoammonium, tertiary organoammonium, quaternary organoammonium, and a combination thereof.

As used herein, "aluminum" refers to aluminum metal, alloys thereof, or a combination thereof, and "magnesium" refers to magnesium metal, alloys thereof, or a combination thereof.

An "aluminum component", as used herein, refers to a component of the heat transfer system that comprises aluminum and/or an aluminum alloy. The component comprises a single aluminum component, or several components comprising at least one aluminum component joined together. The components can be joined together using brazing. In one embodiment, brazing is effected using controlled atmosphere brazing (CAB) in the presence of a fluxing agent comprising halide anions. In another embodiment, the fluxing agent comprises fluoride and chloride anions. In one advantageous embodiment, the fluxing agent comprises fluoride anions.

Certain compounds are described herein using a general formula that includes variables, e.g., R1, R2, X, and the like. Unless otherwise specified, each variable within such a formula is defined independently of other variables.

What is claimed is:

1. A method of transferring heat, comprising:
contacting a heat transfer system comprising an aluminum component, a magnesium component, or an aluminum component and a magnesium component with the heat transfer fluid, the heat transfer fluid comprising:
a hydroxylated carboxylic acid of formula (I):

$$(OH)_x(R^1)(COOH)_y \quad (I),$$

wherein x is 2 to 10, y is 3 to 10, and $R^1$ is a $C_{2-50}$ aliphatic group, a $C_{6-50}$ aromatic group, or a combination thereof; and
wherein the hydroxylated carboxylic acid comprises the hydroxylated carboxylic acid, an ester thereof, a salt thereof, an anhydride thereof, or a combination thereof; and
wherein the heat transfer fluid is free of silicates.

2. The method of claim 1, wherein the heat transfer fluid comprises about 0.01 to 10 weight percent of the hydroxylated carboxylic acid.

3. A method of transferring heat comprising:
contacting a heat transfer system comprising an aluminum component, a magnesium component, or an aluminum component and a magnesium component with the heat transfer fluid, the heat transfer fluid comprising:
a hydroxylated carboxylic acid of formula (II):

$$R^2[R^4(OH)_x(COOH)_{y-z}][R^3(COOH)_z] \quad (II),$$

wherein
$R^2$ is monovalent,
$R^3$ has a total valence of 1+z,
$R^2$ and $R^3$ are independently a $C_{1-20}$ aliphatic group, $C_{6-20}$ aromatic group, or a combination thereof,
$R^4$ has a total valence of 2+x+y-z, and is a $C_{2-15}$ aliphatic group, $C_{6-15}$ aromatic group, or a combination thereof, z is 1 to 8, with the proviso that y-z is greater than or equal to 2, wherein the hydroxylated carboxylic acid comprises the hydroxylated carboxylic acid, an ester thereof, a salt thereof, an anhydride thereof, or a combination thereof; and wherein the heat transfer fluid is free of silicates.

4. The method of claim 3, wherein the hydroxylated carboxylic acid is of formula (III):

$$R^5[R^7(OH)_x(COOH)_{y-z}][R^6(COOH)_z] \quad \text{(III)},$$

wherein $R^5$ and $[R^6(COOH)_z]$ have a total valence of 1, and are independently a $C_{1-20}$ aliphatic group selected from the group consisting of an alkyl group, an alkenyl group, a cycloalkyl group, a cycloalkenyl group, and a combination thereof, $[R^7(OH)_x(COOH)_{y-z}]$ has a total valence of 2, and is a $C_{1-15}$ aliphatic group selected from the group consisting of an alkylene group, an alkenylene group, a cycloalkylene group, a cycloalkenylene group, and a combination thereof.

5. The method of claim 4, wherein the hydroxylated carboxylic acid is of formula (IV):

$$CH_3(CH_2)_m[R^7(OH)_x(COOH)_{y-1}](CH_2)_n(COOH) \quad \text{(IV)},$$

wherein m and n are independently 0 to 19.

6. The method of claim 2, wherein m and n are independently 0 to 15.

7. The method of claim 6, wherein m and n are independently 0 to 10.

8. The method of claim 7, with the proviso that m+n is less than or equal to 16.

9. The method of claim 5, wherein the hydroxylated carboxylic acid is selected from the group consisting of:

a hydroxylated carboxylic acid of formula (V):

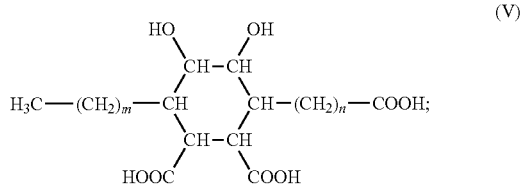

a hydroxylated carboxylic acid of formula (VI):

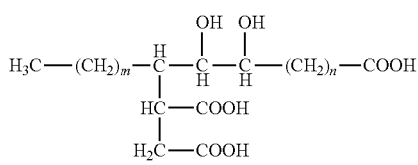

and a combination thereof.

10. The method of claim 9, wherein m and n are independently 0 to 15.

11. The method of claim 10, wherein m and n are independently 0 to 10, with the proviso that m+n is less than or equal to 16.

12. The method of claim 9, wherein the anhydride of the hydroxylated carboxylic acid of formula (V) is of formula (XI):

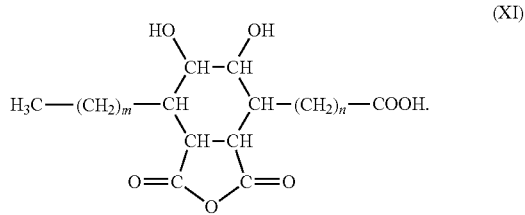

13. The method of claim 1, wherein the ester of the hydroxylated carboxylic acid is of formula (VII):

$$(OH)_x(R^1)(COOH)_{y-p}(COOR^8)_p \quad \text{(VII)},$$

wherein p is 1 to 9, with the proviso that p is less than or equal to y, and $R^8$ is a $C_{1-50}$ hydrocarbyl group.

14. The method of claim 13, wherein $R^8$ is of formula (VIII):

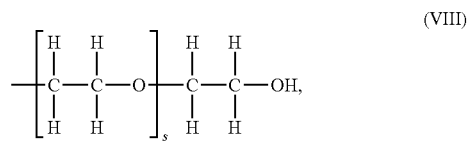

wherein s is 0 to 10.

15. The method of claim 1, wherein the salt of the hydroxylated carboxylic acid is of formula (IX):

$$(OH)_{x-q}(OM)_q(R^1)(COOH)_{y-p}(COOM)_p \quad \text{(IX)},$$

wherein q is 1 to 9, with the proviso that q is less than or equal to x, and M comprises an organic cation, an inorganic cation, or a combination thereof.

16. The method of claim 15, wherein M comprises an alkali metal cation, an alkaline earth metal cation, a transition metal cation, an ammonium cation, a phosphonium cation, a pyridinium cation, an imidazolinium cation, a pyrazolinium cation, a triazolinium cation, a tetrazolinium cation, or a combination thereof.

17. The method of claim 1, wherein the anhydride of the hydroxylated carboxylic acid is of formula (X):

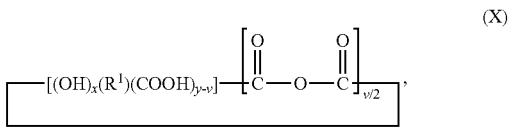

wherein v is 2, 4, 6, 8, or 10, with the proviso that v is less than or equal to y.

18. The method of claim 1, comprising about 0.01 percent by weight to about 10 percent by weight of the hydroxylated carboxylic acid, based on the total weight of the heat transfer fluid.

19. The method of claim 18, comprising about 0.1 percent by weight to about 5 percent by weight of the hydroxylated carboxylic acid, based on the total weight of the heat transfer fluid.

20. The method of claim 1, wherein the heat transfer fluid further comprises a monohydric alcohol, a polyhydric alcohol, or a combination thereof.

21. The method of claim 20, wherein the alcohol is selected from the group consisting of methanol, ethanol, propanol, butanol, furfural, tetrahydrofurfurol, ethoxylated furfural, alkoxy alkanol, ethylene glycol, diethylene glycol, triethylene glycol, 1,2-propylene glycol, 1,3-propylene glycol, dipropylene glycol, butylene glycol, glycerol, glycerol-1,2-dimethyl ether, glycerol-1,3 dimethyl ether, monoethylether of glycerol, sorbitol, 1,2,6-hexanetriol, trimethylol propane, and a combination thereof.

22. The method of claim 1 comprising about 0 to about 99.9 percent by weight of the alcohol, based on the total weight of the heat transfer fluid.

23. The method of claim 1, comprising about 1 to about 60 percent by weight of the water, based on the total weight of the heat transfer fluid.

24. The method of claim 1, further comprising a corrosion inhibitor comprising an azole, a siloxane, a colloidal silica, a $C_6$ to $C_{14}$ aliphatic or aromatic mono- or di-carboxylic acid, a $C_6$ to $C_{14}$ aliphatic or aromatic mono- or di-carboxylate, a tall oil fatty acid, a borate, a nitrate, a nitrite, an alkali metal salt thereof, an alkaline earth metal salt thereof, an ammonium salt thereof, an amine salt thereof, or a combination thereof.

25. The method of claim 1, further comprising an oxyanion of molybdenum, tungsten, vanadium, phosphorus, antimony, or a combination thereof.

26. The method of claim 1, further comprising a colorant, an antifoam agent, a wetting agent, a biocide, a bitterant, a dispersant or a combination thereof.

\* \* \* \* \*